United States Patent [19]

Boucherle et al.

[11] 4,301,167
[45] Nov. 17, 1981

[54] 2-AMINO THIAZOLINE DERIVATIVES

[75] Inventors: Andre L. Boucherle, La Tronche; Marie-Pierre D. Viallet, Grenoble, both of France

[73] Assignee: Institut Merieux, Lyons, France

[21] Appl. No.: 116,304

[22] Filed: Jun. 6, 1979

[30] Foreign Application Priority Data

Oct. 24, 1977 [FR] France .................. 77 31933

[51] Int. Cl.³ ............................ C07D 277/18
[52] U.S. Cl. .................... 424/270; 548/190; 548/193; 548/195; 548/196
[58] Field of Search .............. 548/196, 195, 190, 193; 424/270

[56] References Cited

U.S. PATENT DOCUMENTS

| 3,959,304 | 5/1976 | Teach | 548/200 |
| 4,072,688 | 2/1978 | Teach | 548/200 |
| 4,105,773 | 8/1979 | Crossley et al. | 424/270 |

Primary Examiner—Nicholas S. Rizzo

Attorney, Agent, or Firm—Cushman, Darby & Cushman

[57] ABSTRACT 2-amino thiazoline derivative having Formula I:

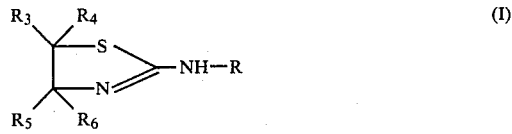

wherein:

R represents —R$_1$ or —CO—R$_2$, wherein R$_1$ represents benzyl monosubstituted in the ortho position by lower alkoxy or in the ortho, meta or para position by lower alkyl, trifluoromethyl or halogen, or R$_1$ represents cycloalkylmethyl; and R$_2$ represents cycloalkyl, naphthyl, styryl or substituted phenyl; and R$_3$, R$_4$, R$_5$ and R$_6$, each independently represent hydrogen or lower alkyl.

The said 2-amino thiazoline is useful as a medicine in the preparation of pharmaceutical compositions.

13 Claims, No Drawings

2-AMINO THIAZOLINE DERIVATIVES

The present invention relates to 2-amino thiazoline derivatives and to pharmaceutical compositions containing them.

More specifically, the present invention relates to 2-amino thiazoline derivatives having the following formula I:

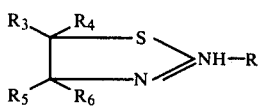

wherein:
R represents $-R_1$ or $-CO-R_2$, wherein $R_1$ represents benzyl monosubstituted in the ortho position by lower alkoxy or in the ortho, meta or para positions by lower alkyl, trifluoromethyl or halogen, or $R_1$ represents cycloalkylmethyl wherein the cycloalkyl moeity has 5 or 6 chains; and $R_2$ represents cycloalkyl, naphthyl, styryl, or substituted phenyl; and $R_3$, $R_4$, $R_5$ and $R_6$, each independently represent hydrogen or lower alkyl.

The present invention also relates to the pharmaceutically acceptable acid addition salts of the 2-amino thiazoline derivatives of Formula I.

In Formula I, the lower alkyl or lower alkoxy substituents preferably have from 1 to 4 carbon atoms; the halogen substituent is fluorine, chlorine or bromine; the cycloalkyl substituent preferably has 5 or 6 chains; when $R_2$ represents substituted phenyl, the phenyl moiety is mono or disubstituted by halogen, lower alkyl or lower alkoxy, trifluoromethyl or nitro; the substituent or substituents can occupy the para position, the meta position or, preferably, the ortho position.

The present invention particularly relates to the 2-amino thiazoline derivatives of Formula I wherein $R_3 = R_4 = R_5 = R_6 =$ hydrogen and to those derivatives wherein one of the pairs ($R_3$, $R_4$) or ($R_5$, $R_6$) represents

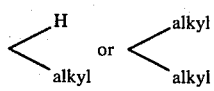

and the other represents two atoms of hydrogen.

The compounds of Formula I, as well as their addition salts, possess interesting pharmacological properties. In particular, they provide antiinflammatory activity. Furthermore, certain ones of them possess analgesic activity.

The compounds of the present invention can be used, for example, in the treatment of rheumatic ailments; arthroses; lumbago; muscular, articulatory or nervous pains; toothaches; shingles; migraines; and in the form of supplementary treatments, they can be used for infectious and feverish conditions.

Thus in the field of medicine, the present invention relates to therapeutically active compounds of Formula I, as well as their pharmaceutically acceptable acid addition salts.

More particularly, the present invention relates to medicines containing the compounds of Formula I which are described below in Examples 1 through 24.

The pharmaceutically acceptable addition salts are specifically those formed by the amines of Formula I ($R=R_1$) with hydrochloric, fumaric, maleic, oxalic, citric or succinic acid.

The present invention includes the pharmaceutical compositions containing at least one of the compounds described above as an active constituent, which is generally present in an amount between 0.5 and 30 percent by weight of said composition.

These compositions can be administered, preferably orally or rectally; or locally by topical application on the skin or the mucous membranes. Thus, they can be provided in the form of a powder, granules, tablets, lozenges, pills, capsules, solutions, drinkable suspensions or emulsions, creams, lotions, ointments or suppositories.

In addition to this active constituent, the pharmaceutical compositions of the present invention contain a pharmaceutical excipient so as to provide the composition in a form suitable for oral, rectal or local administration. The pharmaceutical excipient includes liquid dilution agents such as, for example, water, alcohol and oils, solid powdery dilution agents, binding agents, lubricating agents, etc. or other commonly-used adjuvants, on the condition that they are compatible with the 2-amino thiazoline derivatives of Formula I. Representative dilution agents or other commonly employed excipients include, for example, sucrose, lactose, glucose and starch; representative binding agents include, for example, gum arabic, gelatin and gum tragacanth; representative lubricating agents include, for example, stearic acid, talc, magnesium stearate and similar products.

These pharmaceutical composition forms are prepared in accordance with usual or conventional methods.

The dosage can vary according to the particular method of administration, the body weight and the therapeutic effect sought. For example, the dosage for adults can vary between 0.250 gm and 3 gm of active component per day.

The present invention also relates to a process for treating pain and inflammatory ailments, comprising administering, to a human being or an animal, a sufficient amount of at least one 2-amino thiazoline derivative of Formula I, as described above. Specifically, the 2-amino thiazoline derivative is administered in the form of a pharmaceutical composition described above.

The present invention is also related to a process for preparing the compounds of Formula I.

This process comprises:

(a) reacting an acid chloride of the formula, $R_2COCl$, with a 2-amino thiazoline of Formula II:

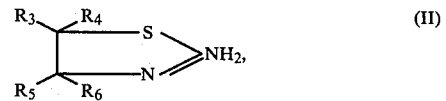

one mole of said acid chloride being reacted with two moles of said 2-amino thiazoline, and then isolating the resulting amide having Formula I above wherein $R=-CO-R_2$; or (b) reacting 2-amino thiazoline of Formula II with an acid chloride of the formula $R'_1COCl$, wherein $R'_1$ is a group such that the radical $-CH_2-R'_1$ is identical to $R_1$ as defined above; two moles of said 2-amino thiazoline being reacted with one mole of said acid chloride, and then subjecting the resulting amide having the formula:

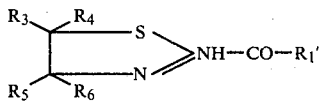

to a reducing agent capable of reducing the carbonyl group of the said amide to a methylene group, thereby yielding a 2-amino thiazoline derivative of Formula I wherein $R=R_1$; or (c) reacting an amino-alcohol having Formula IV:

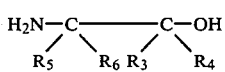

wherein $R_3$, $R_4$, $R_5$ and $R_6$ have the meanings given above with an isothiocyanate of the Formula V:

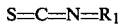

wherein $R_1$ is defined above, thereby obtaining a 2-amino thiazoline derivative of Formula I wherein $R=R_1$.

The amino thiazolines of Formula II, above, can be prepared, specifically, in accordance with the procedure described in U.S. Pat. No. 2,345,208.

The reaction of the acid chlorides with the 2-amino thiazoline is preferably carried out in anhydrous benzene.

In order to reduce the amides of Formula III to the corresponding amine, the hydride of lithium and aluminum ($LiAlH_4$) is preferably employed as the reducing agent.

The following non-limiting examples illustrate the present invention.

(a) To prepare the compounds of Formula I, 0.1 mole of 2-amino thiazoline and 50 cc of anhydrous benzene are poured into the reaction vessel. There is then added, drop by drop, while agitating, 0.05 mole of the desired acid chloride in 50 cc of anhydrous benzene. After the addition is completed, agitation is continued for four hours at ambient temperature. Occasionally, it is necessary to heat to reflux for several hours.

By filtration, the precipitate formed and the filtrate are separated. The precipitate is washed with distilled water, dried and purified in ethanol. The corresponding amide of Formula I is thus obtained.

A part of the amide in the filtrate can be recovered by washing it with a solution of 10 percent sodium carbonate and then with water, after which the solvent is dried and evaporated under reduced pressure. The residue, purified by recrystallization in ethanol, provides a second stream of the desired amide.

The following amides were prepared by the foregoing procedures:

TABLE I

| Examples | Amide of Formula I | Melting Point (°C.) |
|---|---|---|
| 1 | (p-chlorobenzoyl) 2-amino thiazoline | 221 |
| 2 | (p-toluoyl) 2-amino thiazoline | 225 |
| 3 | (p-bromobenzoyl) 2-amino thiazoline | 221–222 |
| 4 | (m-toluoyl) 2-amino thiazoline | 160 |
| 5 | (2',6'-dichloro benzoyl) 2-amino thiazoline | 137 |
| 6 | (o-toluoyl) 2-amino thiazoline | 155–156 |
| 7 | (m-trifluoromethylbenzoyl) 2-amino thiazoline | 163–164 |
| 8 | (o-trifluoromethylbenzoyl) 2-amino thiazoline | 195 |
| 9 | (2',6'-xyloyl) 2-amino thiazoline | 131–133 |
| 10 | (o-chlorobenzoyl) 2-amino thiazoline | 188.5–189 |
| 11 | (cyclohexylcarbonyl) 2-amino thiazoline | 172–173 |
| 12 | (naphthoyl-1) 2-amino thiazoline | 165–166 |
| 13 | (p-nitrobenzoyl) 2-amino thiazoline | 261–262 |
| 14 | (o-methoxybenzoyl) 2-amino thiazoline | 154–154.5 |
| 15 | cinnamoyl 2-amino thiazoline | 168.5–169.5 |

(b) The derivatives of Formula I described below were prepared in accordance with the following procedures.

0.025 mole of lithium-aluminum hydride and 0.0125 mole of the amide of Formula III above in 200 cc of ethyl ether are mixed and agitated at reflux temperature for two hours. After cooling, the excess hydride is destroyed with 30 cc of water by cooling to 0° C.

The precipitate is separated by decantation, extracted with ether, the ether stages are combined and dried on sodium sulfate and evaporated. under reduced pressure.

The residue is purified by recrystallization in hexane.

The following derivatives of Formula I were prepared in this manner:

TABLE II

| Examples | Amine of Formula I | Melting Point (°C.) |
|---|---|---|
| 16 | (p-chlorobenzyl) 2-amino thiazoline | 108 |
| 17 | (p-methylbenzyl) 2-amino thiazoline | 105 |
| 18 | (p-bromobenzyl) 2-amino thiazoline | 101 |
| 19 | (o-methylbenzyl) 2-amino thiazoline | 123–123.5 |
| 20 | (m-trifluoromethylbenzyl) 2-amino thiazoline | 70–71 |
| 21 | (o-chlororbenzyl) 2-amino thiazoline | 104.5 |
| 22 | (cyclohexylmethyl) 2-amino thiazoline | 102–102.5 |
| 23 | (α-naphthylmethyl) 2-amino thiazoline | 155.5–156.5 |
| 24 | (o-methoxybenzyl) 2-amino thiazoline | 97–99 |

The addition salts of these amines are prepared in accordance with conventional procedures.

As indicated above, the compounds of Formula I exhibit anti-inflammatory and analgesic properties which are particularly illustrated in the following tests:

(1) Test of the carrageen abcess: Benitz and Hall, Arch, and Int. Pharmacod, 1963, 144, 185.

(2) Test of the carrageen edema. This test is performed in the following manner:

The test is for the protection against abdominal cramps produced in mice by the intraperitoneal injection of BPQ (phenylbenzoquinone). This analgesic activity test is described by Siegmun and colleagues, Proc. Soc. Exp. Biol. Med., 1957, 95, 729–731.

By injection of 0.05 ml of an aqueous suspension of 1 percent carrageen in the plantar aponeurosis of the left rear paws of male rats having an average weight of from 150 to 175 gm, an edema is formed. The volume of the paws is measured with a plethysmograph at 0, 2, 4, 6 and 24 hours, with the hour 0 being the hour of the carrageen injection.

One hour before the injection of carrageen (preventive treatment) or two hours after the injection of carrageen (curative treatment), the animals being treated received the compound under study orally.

The control animals only received the solvent, under the same conditions.

The development of the volume of the paws is recorded graphically as a function of time and, for each dose, the percentage of inhibition of the edema is calculated by comparison with the maximum edema observed in the control animals.

The investigation of contingent ulcerogenic effect was carried out in accordance with the test described by P. Boissier and colleagues, *Therapie*, 1967, Vol. 22, pages 157–168. The products of Formula I have a slight ulcerogenic effect when it is compared with that of phenylbutazone.

EXAMPLES OF THE PREPARATION OF PHARMACEUTICAL COMPOSITION

Example I 500-mg tablets having the following composition were prepared:

| Product of Example 6 | 0.100–0.150 gm |
|---|---|
| Excipient (starch, talc, magnesium stearate) sufficient for | 0.5 gm |

Example II

An ointment for local application having the following composition was prepared:

| Product of Example 18 | 1–1.5 gm |
|---|---|
| Excipient (lanolin and petrolatum) sufficient for | 100 gm |

What is claimed is:

1. 2-amino thiazoline derivative having the Formula I:

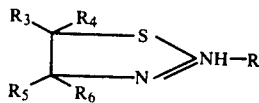

wherein:
R represents $-R_1$ or $-CO-R_2$, wherein $R_1$ represents benzyl monosubstituted in the ortho position by lower alkoxy or in the ortho, meta or para position by lower alkyl, trifluoromethyl or halogen, or $R_1$ represents cycloalkylmethyl wherein the cycloalkyl moiety has 5 or 6 chains; and $R_2$ represents cycloalkyl, naphthyl, styryl or substituted phenyl, the phenyl moiety being monosubstituted or disubstituted by halogen, lower alkyl, lower alkoxy, trifluoromethyl or nitro; and $R_3$, $R_4$, $R_5$ and $R_6$, each independently represent hydrogen or lower alkyl group.

2. The derivative of claim 1, wherein $R_3 = R_4 = R_5 = R_6 =$ hydrogen.

3. The derivative of claim 1, wherein one of the pairs ($R_3$, $R_4$) or ($R_5$, $R_6$) represents

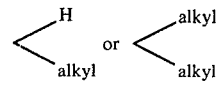

and the other represents two atoms of hydrogen.

4. The derivative of claim 1 selected from the derivative wherein R represents $R_1$, and an addition salt thereof.

5. The derivative of claim 1, wherein the lower alkyl or lower alkoxy has 1 to 4 carbon atoms, the halogen is fluorine, chlorine or bromine and the cycloalkyl has 5 or 6 chains.

6. The derivative of claim 1 wherein R is $-CO-R_2$ and $R_2$ represents cycloalkyl, naphthyl, styryl or substituted phenyl, the phenyl moiety being monosubstituted or disubstituted by halogen, lower alkyl, lower alkoxy, trifluoromethyl or nitro.

7. The derivative of claim 6, wherein the substituent occupies the ortho position.

8. The derivative of claim 1 selected from the group consisting of (p-chlorobenzoyl) 2-amino thiazoline; (p-toluoyl) 2-amino thiazoline; (p-bromobenzoyl) 2-amino thiazoline; (m-toluoyl) 2-amino thiazoline; (2',6'-dichlorobenzoyl) 2-amino thiazoline; (o-toluoyl) 2-amino thiazoline; (m-trifluoromethyl-benzoyl) 2-amino thiazoline (o-trifluoromethylbenzoyl) 2-amino thiazoline; (2',6'-xyloyl) 2-amino thiazoline; (o-chlorobenzoyl) 2-amino thiazoline; (cyclohexylcarbonyl) 2-amino thiazoline; (naphthoyl) 2-amino thiazoline; (p-nitrobenzoyl) 2-amino thiazoline; (o-methoxybenzoyl) 2-amino thiazoline; and cinnamoyl 2-amino thiazoline.

9. A derivative selected from the group consisting of (p-chlorobenzyl) 2-amino thiazoline; (p-methylbenzyl) 2-amino-2 thiazoline; (p-bromobenzyl) 2-amino thiazoline; (o-methylbenzyl) 2-amino thiazoline; (m-trifluoromethylbenzyl) 2-amino thiazoline; (o-chlorobenzyl) 2-amino thiazoline; (cyclohexylmethyl) 2-amino thiazoline; (α-naphthylmethyl) 2-amino thiazoline; (o-methoxybenzyl) 2-amino thiazoline and the addition salts thereof.

10. A therapeutically active compound as claimed in claims 1 or 9 as a medicine for the treatment of pain and inflammatory ailments.

11. A pharmaceutical composition containing at least one compound as defined in claims 1 or 9 as an active constituent for the treatment of pain and inflammatory ailments.

12. A process for the treatment of pain and inflammatory ailments, comprising administering an effective amount of at least one compound as defined in claims 1 or 9 to a human being or an animal.

13. (o-toluoyl) 2-amino thiazoline.

* * * * *